United States Patent [19]

Craig et al.

[11] 3,971,946

[45] July 27, 1976

[54] X-RAY APPARATUS WITH IMPROVED HOUSING FOR COMPONENTS

[75] Inventors: James R. Craig, Glenview; George W. Otto, Jr., Elmhurst, both of Ill.

[73] Assignee: American Radiologic Systems Inc., Melrose Park, Ill.

[22] Filed: Dec. 12, 1974

[21] Appl. No.: 532,013

[52] U.S. Cl. .................. 250/422; 250/415
[51] Int. Cl.² .......................... H05G 1/10
[58] Field of Search .......... 250/402, 413, 416, 422, 250/491, 450, 415

[56] References Cited
UNITED STATES PATENTS

| | | | |
|---|---|---|---|
| 1,586,027 | 5/1926 | Campbell | 250/422 |
| 1,941,978 | 1/1934 | Fayer | 250/422 |
| 1,957,436 | 5/1934 | Wantz | 250/422 |
| 2,894,143 | 7/1959 | Graves | 250/422 |
| 3,061,729 | 10/1962 | Craig | 250/413 |
| 3,130,312 | 4/1964 | Craig | 250/413 |
| 3,302,022 | 1/1967 | Brenner et al. | 250/449 |
| 3,838,287 | 9/1974 | Barrett et al. | 250/490 |

*Primary Examiner*—Alfred E. Smith
*Assistant Examiner*—B. C. Anderson
*Attorney, Agent, or Firm*—Olson, Trexler, Wolters, Bushnell & Fosse, Ltd.

[57] ABSTRACT

An X-ray apparatus with improved housing of components comprises a pedestal with an X-ray table thereon, and power components of the apparatus housed within the pedestal. Those power components comprise the high voltage X-ray transformer and the power control for the same. An operator's control unit is remote from the pedestal and is connected to components within the pedestal by a low voltage cable. The control unit may be mounted on a table, wall, or other suitable location. The control unit contains the components that the X-ray technician needs to select the factors that determine the X-ray exposure.

8 Claims, 3 Drawing Figures

X-RAY APPARATUS WITH IMPROVED HOUSING FOR COMPONENTS

BACKGROUND OF THE INVENTION

This invention relates to improvements in diagnostic X-ray apparatus, and more particularly to an improved arrangement for housing the components of such apparatus.

A typical diagnostic X-ray apparatus includes a table for supporting the patient and a pedestal or similar upright structure upon which the table is mounted. The apparatus also generally includes a tube stand for supporting an X-ray tube which cooperates with a bucky grid and film carrier below the table whereby a bucky radiograph can be made.

The apparatus also includes a high voltage transformer. The secondary winding of this transformer supplies the operating voltage to the X-ray tube. In addition, a suitable power control means is used to apply the necessary voltage of proper magnitude and duration to the primary winding of the high voltage transformer. This power control unit may include an autotransformer, relays, switches, X-ray timer and other components necessary for the X-ray technician to select and monitor the proper X-ray exposure.

In apparatus of the foregoing type the high voltage transformer and power control means are generally housed separately and externally of the table. The housing for the X-ray transformer and the cabinet for the power control means have tended to take up an excessively large amount of space, often in a separate shielded room or booth. Furthermore, apparatus of the foregoing type has frequently necessitated extensive on-site construction, which tends to be disruptive to medical personnel as well as being costly. In fact, the cost and construction problems involved in installation of some types of diagnostic X-ray apparatus has been an inhibiting factor in physicians purchasing such equipment.

More particularly with regard to the foregoing, the usual interconnection of the components of the apparatus has been through power conduits and raceways. High voltage cables have had to be run through very expensive raceways from the X-ray transformer to the tube. Interconnecting these components through conduits and raceways requires the services of highly skilled engineers. Moreover, where new and more sophisticated apparatus is to replace old apparatus, stripping of the equipment rooms and almost complete remodeling is often required.

OBJECTS AND SUMMARY OF THE INVENTION

It is an object of this invention to provide an X-ray apparatus in which the high voltage X-ray transformer and power control means are housed within the pedestal that supports the table, leaving only the necessity for an external control unit remote from the table for use by the technician in selecting the necessary factors to determine the X-ray exposure.

It is a futher object of this invention to provide an apparatus of the type stated in which the external control unit is connected to the components within the pedestal by a low voltage cable, such as a flexible cable, whereby the external control unit can be mounted on a table, wall, or in any other location. For this purpose the control unit is made relatively small.

A still further object of this invention is to provide an X-ray apparatus which eliminates the need for expensive conduits and raceways, thereby reducing the on-site installation cost and the overall cost of the equipment to the purchaser.

Another object of this invention is to provide an X-ray apparatus which is reasonably compact in that the apparatus occupies less space than does comparable apparatus that is currently available commercially. The apparatus of the present invention is particularly suitable for clinics and medical offices where the need is for emergency, screening or general radiography. In these situations fluoroscopy and other specialized procedures are not done.

In accordance with the foregoing objects a preferred embodiment of the present invention comprises a table that is movable on a pedestal, a tube stand mounted for movement longitudinally of the table and carrying an X-ray tube, and a bucky grid and film carrier below the table top. The X-ray power unit is housed within the pedestal. This power unit and control means includes a high voltage transformer, the secondary winding of which provides voltage in the order of kilovoltage to the X-ray tube. The power unit and control means also includes an additional transformer that provides a supply voltage for the primary winding of the high voltage transformer, and switch means for opening and closing the circuit from the additional transformer to said primary winding. Externally of the pedestal there is a remote control unit which has suitable circuitry for initiating a cycle of operation that includes the closing and opening of the switch means, thereby to produce the desired X-ray exposure. An electrical cable connects the control unit to the power unit and control means. The voltage in the cable and across components in the control unit is relatively low, namely not in excess of about 30 volts. This makes the control unit and the cable safe to handle and avoids the necessity of having high voltage lines extending from a remote X-ray transformer to the X-ray tube. In the present invention the high voltage lines go directly from the transformer up along the tube stand to the X-ray tube. Likewise, the power supply line from the electrical outlet in the room in which the apparatus is located need go only to the pedestal rather than to remote components. Considered from another point of view, the invention involves splitting up the power unit and control means so that the power circuits are housed separately and in the table pedestal along side of the high voltage transformer. The operator control unit may then be remote from the table and connected to the power unit via the low voltage telephone type cable that does not have to be installed in any conduit.

DETAILED DESCRIPTION

Figure 1:
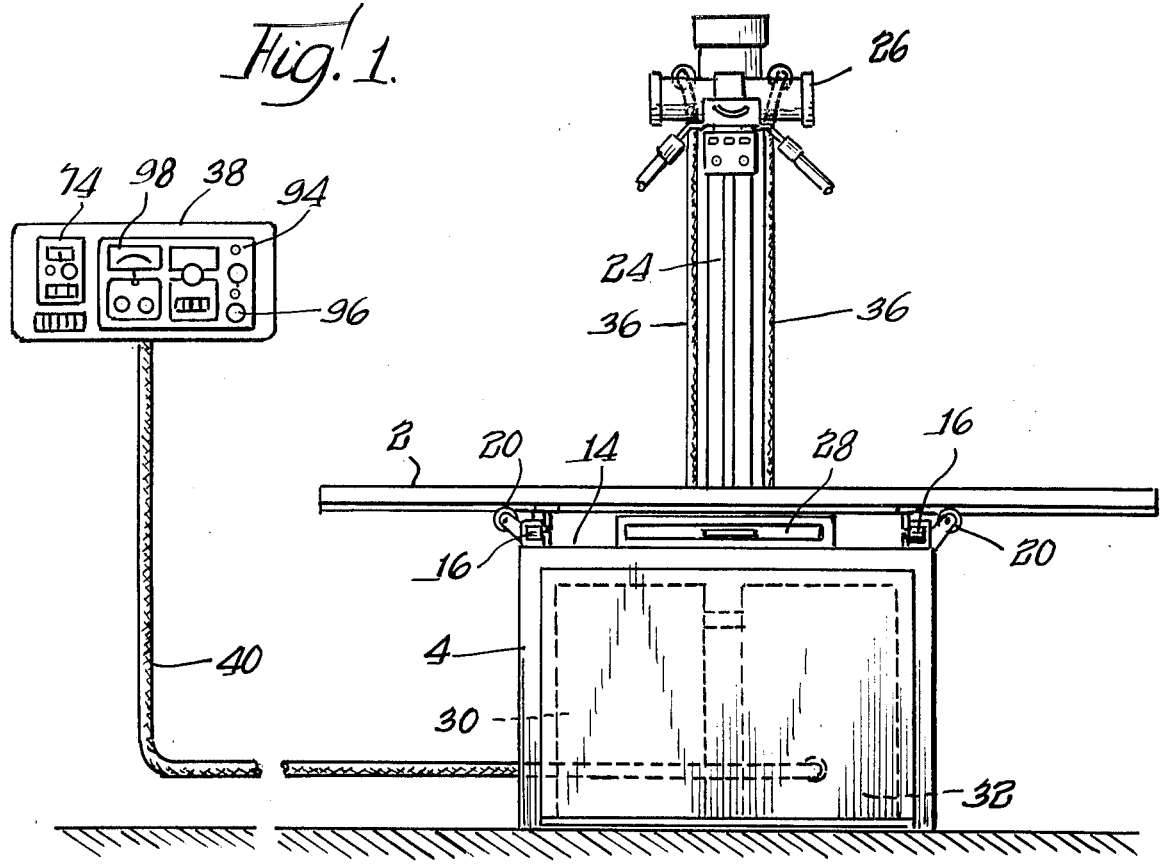
FIG. 1 is a front elevational view of an X-ray apparatus embodying the present invention.
Figure 2:
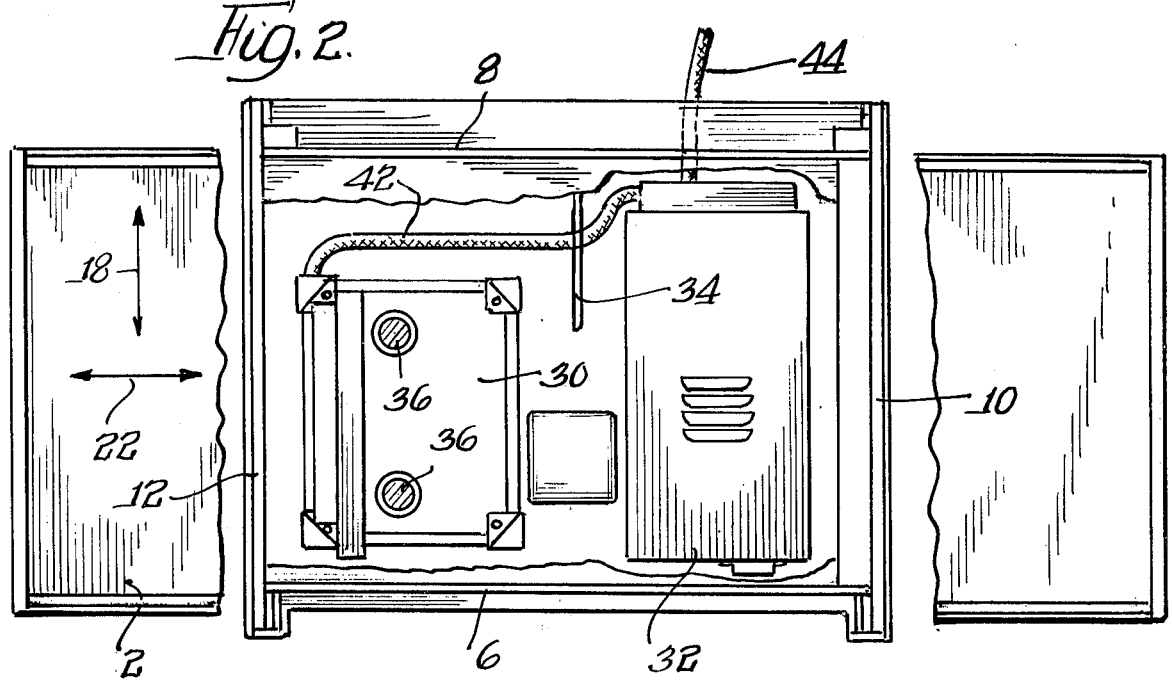
FIG. 2 is an enlarged fragmentary top plan view of the apparatus with parts broken away for purposes of clarity.

Referring now in more detail to the drawing, and particularly to FIGS. 1 and 2, there is shown an X-ray apparatus having a table 2 and a pedestal. The pedestal 4 is adapted to rest on the floor of the room in which the apparatus is installed whereby the table 2 is positioned at a pre-determined height above the level of the floor. The pedestal 4 has front and rear walls 6, 8, sidewalls 10, 12, and a top wall 14. The several walls of the pedestal 4 define an enclosure for purposes presently more fully appearing.

The top wall 14 is provided with tracks for supporting rollers 16 that permit the table 2 to be moved transversely of the pedestal, namely in the two directions shown by the arrow 18 in FIG. 2. Likewise, rollers 20 may be provided on the pedestal for permitting the table 2 to be moved longitudinally, namely, in the directions shown by arrow 22 in FIG. 2. The roller arrangement just described is illustrated somewhat schematically as it is merely intended to represent any suitable arrangement for supporting the table 2 for longitudinal and transverse movement relative to pedestal 4. A variety of known mounting arrangements for this purpose are known in the art and may be suitable for purposes of the present invention.

The apparatus also includes a tube stand 24 which projects upwardly above the top of the table and is adapted to support an X-ray tube 26 at its upper end. The X-ray tube 26 and its housing is conventionally adapted to be moved vertically relative to the frame of the tube stand 24. Below the table 2 is a bucky grid and X-ray film carrier 28 which is adapted to be movable with the tube stand longitudinally and transversely of the table in a manner known in the art.

Mounted within the pedestal 4 are two separate and distinct housings 30, 32 each of which may be of the rectilinear shapes shown in FIGS. 1 and 2, although such configurations are not limiting as far as the present invention is concerned. These housings 30, 32 are on opposite sides of a short divider plate 34 which is a structural part of the pedestal 4. The housings 30, 32 may be secured in a suitable manner either to the floor of the pedestal or to the floor of the examination room in which the equipment is located.

Generally speaking the housings 30, 32 contain the X-ray power unit and control means, or as is sometimes referred to the high voltage X-ray transformer and the power control for the same. The components across which there are kilovoltages and power control voltages are confined within the pedestal except for the high voltage cables 36, 36 which extend through the back wall 8 of the pedestal and upwardly along the tube stand 24 for connection to the X-ray tube 26. The low voltage or operator control for the apparatus is a control unit 38 that is remote from the pedestal 4 and is connected to circuit components in the housing 32 via a low voltage cable 40. The voltage in this cable 40 and across the components within the control unit 38 is not in excess of about 30 volts and preferably of the order of 24 volts. A short connecting cable 42 joins components within the housings 30, 32 while a cable 44 extends through a wall of the pedestal and constitutes a power supply cable for external connection to the power supply (e.g. 220 volts) for the apparatus.

The control unit 38 is a relatively small compact unit containing the necessary controls for effecting the X-ray exposure. This control unit may be mounted on a wall, table, or in any other suitable location within the X-ray examination room or externally thereof. Because the unit 38 and cable 40 operate at a low voltage, it is not necessary to provide any separate channel or raceway for the cable 40, thereby facilitating the installation of the control unit 38.

Figure 3:
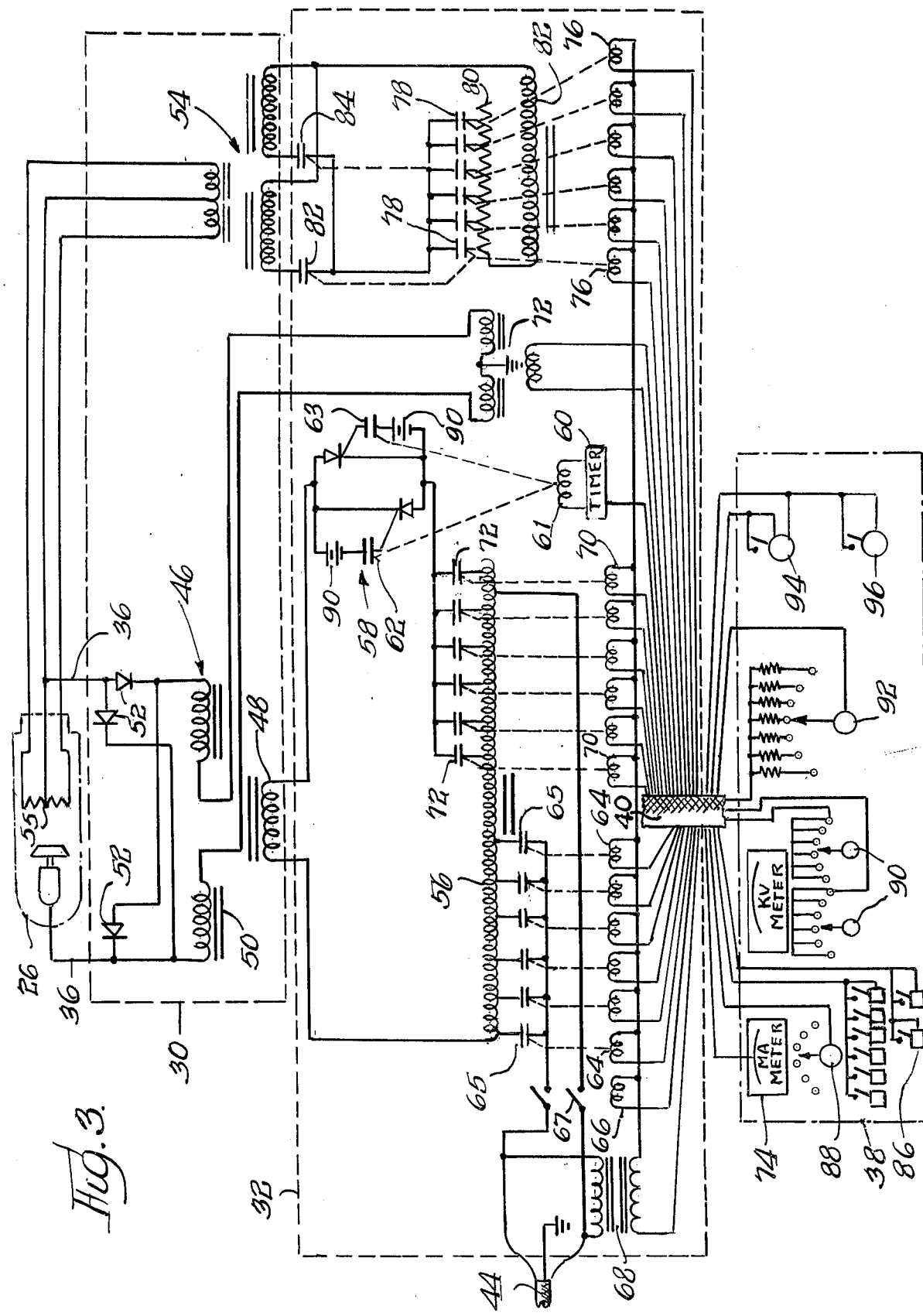
FIG. 3 is a schematic showing circuitry embodied in the X-ray apparatus.

Referring now to FIG. 3 there is shown various components that are within the control unit 38, the housing 30, and the housing 32. More particularly, the housing 30 contains the high voltage or X-ray transformer 46 having a primary winding 48 and a secondary winding 50, the latter providing operating voltage in the order of kilovoltage to the X-ray tube 26. The output of the secondary 50 of the X-ray transformer is connected through the rectifier arrangement 52 shown, which rectifier arrangement is also within the housing 30. The high voltage leads 36, 36 supply direct current to the X-ray tube 26, which may be of the rotating anode type. Also within the housing 30 are the primary and secondary windings of the filament transformer 54. The secondary of the transformer supplies current to the filament 55 of the X-ray tube.

The housing 32, containing the power control circuitry, includes an additional transformer, namely an autotransformer 56 for providing a supply voltage for the primary winding 48. This supply voltage is applied through SCR switch 58 of known design, which switch 58 is opened and closed by a timer 60 in accordance with the duration of the X-ray exposure. The timer 60 includes conventional circuitry and a relay coil 61 that operates contacts 62, 63 in conjunction with the other circuitry of the switch 58, the components being shown connected as in FIG. 3.

Also within the housing 32 is a series of line voltage adjustment relays 64 which control or operate their respective contacts 65 whereby to apply the desired voltage to the "primary" of the autotransformer 56 through the taps at which the contacts 65 are connected. A line on-off relay 66 operates contacts 67 to apply line voltage to the autotransformer. An isolation transformer 68 reduces to about 24 volts the voltage applied to the relay coils, 64, 66 as well as to the other relay coils connected thereto, as shown in FIG. 3, and as will hereinafter be more fully described.

On the "secondary" side of the autotransformer 56 there are taps at which relay contacts 72 are adapted to be selectively placed in series with the SCR switch 58. For this purpose a series of kilovoltage adjustment relays 70 operate their respective contacts 72 for purposes of selecting the proper voltage to be applied to the primary 48 of the X-ray transformer.

Also within the housing 32 is an MA meter selection transformer 72, one winding of which is connected to the secondary 50. The other winding is connected to a MA meter 74 on the control unit 38. The transformer 72 operates in conjunction with conventional circuitry and the meter 74 to measure the X-ray tube current during exposure. X-ray tube current metering circuits are known and need not be described in detail. Suffice it to say that one suitable circuit may be found in United States Patent to Craig U.S. Pat. No. 3,061,729.

Also found within the housing 32 are MA selector relays, the coils 76 of which are adapted to operate respective relay contacts 78. The relay contacts 78 tap off of a resistor 80 at the output of a filament supply transformer 82. In a typical arrangement the left hand three relays 76 are adapted to operate another pair of contacts 82 while the right hand three relays 76 are adapted to operate further contacts 84 plus the contacts 82. This arrangement is conventional and provides for the appropriate voltage to be applied to the filament transformer 74 in accordance with a large or small focus that may be desired from the X-ray tube.

Such circuit arrangement is conventional, need not be described further in detail herein.

The foregoing components of the power control, housed within the housing 32 as shown in FIG. 3, are connected via the low voltage cable 40 to operator controls, such as suitable switches, on the control unit 38. Thus, the various lead wires from the relay coils 76, transformer 72, timer 60, relay coils 70, 64, 66 and transformer 68 are all cabled together to make up the wires of the cable 40. The conductors constituting outputs from components within the housing 32 are made of the connections to the primary 48, the connection from secondary 50 to the transformer 72, and the connections from the contacts 82, 84 to the transformer 54, all of which are cabled together to form the short connecting cable 42 that is within the pedestal 4.

The control unit 38 includes a line on-off switch 86 for operating the line on-off relay 66. In addition there is a line voltage adjustment switch 88 for selectively operating any one of the line voltage adjustment relay coils 64. Selector switches 90 may be operated to selectively adjust the kilovoltage, namely by selectively operating anyone of the relay coils 70. Selector switch 92 is a time selector switch operating in conjunction with the X-ray timer circuitry, the low voltage portions of which are in the control unit 38 and higher voltage portions of which are in the housing 32. The timer circuit may be of any known type, for instance, that shown in United States Patent to Craig 3,130,312.

Also forming part of the control unit 38 are exposure controls 94, 96. These operate in conjunction with other components in the control unit to initiate a cycle of operation that includes the opening and closing of the SCR switch 58. For example, the exposure control 94 may operate one of the selected relay coils 86 and may also start the anode of the X-ray tube rotating preparatory to commencing the exposure. The switch 96 may activate the SCR switch for subsequent operation as by turning on d.c. power supplies 90, 90 that form part of the SCR switch. Also, the switch 96 initiates the exposure as by starting the timer 60.

Thus, the remote operator control unit 38 includes the line on-off, remote tap changers for line voltage adjustment and kilovoltage, the relays 64, 70 and their associated contacts 65, 72, remote milliampere and time selectors, and remote X-ray exposure control. These functions give the operator control of the operation of the X-ray tube and at the same time the arrangement avoids the necessity of having high voltage cables outside of the pedestal, except for the cables 36 to the X-ray tube 26. A kilovoltage meter 98 may also be on the control unit adjacent to the switches 90.

The invention is claimed as follows:

1. X-ray apparatus comprising a pedestal, a table on said pedestal and movable thereon, a tube stand mounted for movement longitudinally of said table and carrying and X-ray tube, a bucky grid and X-ray film carrier below the table and movable with the tube stand, X-ray power unit and control means both housed within the pedestal so as to underlie the table; said power unit having components including a high voltage transformer having a primary winding and a secondary winding for providing operating voltage in the order of kilovoltage to said X-ray tube, said control means having components including an additional transformer providing a supply voltage for said primary winding, and said control means further having switch means for opening and closing a circuit from said additional transformer to said primary winding; means forming a conductive connection between components of the power unit and components of the control means, a control unit remote from said pedestal and having means including timer circuitry for initiating a cycle of operation that includes the closing and opening of said switch means, thereby to produce an X-ray exposure, said switch means and a part of said timer circuitry being in the housing in which said additional transformer is located, and an electrical cable connecting said control unit to said control means, the voltage in said cable and across components in said control unit being not in excess of about 30 volts.

2. X-ray apparatus according to claim 1 in which said additional transformer is an autotransformer.

3. X-ray apparatus according to claim 2 in which the two transformers are in separate housings in the pedestal.

4. X-ray apparatus according to claim 3 in which a conductive cable constituting said conductive connection extends between the separate housings.

5. X-ray apparatus according to claim 1 in which the part of the timer circuitry that is in said control unit comprises time selector means.

6. X-ray apparatus according to claim 5 in which said control unit further includes X-ray tube current selector switch means and X-ray tube voltage selector switch means.

7. X-ray apparatus according to claim 1 in which said two transformers are in separate housings within the pedestal and said pedestal has walls forming an enclosure.

8. X-ray apparatus according to claim 7 in which the housing for the high voltage transformer also contains a filament transformer having a secondary connected to the filament of the X-ray tube.

* * * * *

UNITED STATES PATENT AND TRADEMARK OFFICE
CERTIFICATE OF CORRECTION

PATENT NO. : 3,971,946
DATED : July 27, 1976
INVENTOR(S) : James R. Craig, George W. Otto, Jr.

It is certified that error appears in the above-identified patent and that said Letters Patent are hereby corrected as shown below:

Col. 2, lines 20 & 21, change to read:  --table top. The X-ray power unit and control means is housed within the pedestal. This power unit includes a ---

Col. 6, line 4, "and" should be --an--

Signed and Sealed this

Twenty-sixth Day of October 1976

[SEAL]

Attest:

RUTH C. MASON
*Attesting Officer*

C. MARSHALL DANN
*Commissioner of Patents and Trademarks*